US010729627B2

(12) United States Patent
Court et al.

(10) Patent No.: US 10,729,627 B2
(45) Date of Patent: *Aug. 4, 2020

(54) ANHYDROUS ANTIPERSPIRANT COMPOSITIONS

(71) Applicant: Conopco, Inc., Englewood Cliffs, NJ (US)

(72) Inventors: Duncan Alexander Court, Wallasey (GB); Kevin Ronald Franklin, Wirral (GB); Philip Christopher Waterfield, Heswall (GB)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/512,040

(22) Filed: Jul. 15, 2019

(65) Prior Publication Data

US 2019/0343741 A1    Nov. 14, 2019

Related U.S. Application Data

(63) Continuation of application No. 15/520,652, filed as application No. PCT/EP2015/074528 on Oct. 22, 2015, now Pat. No. 10,398,633.

(30) Foreign Application Priority Data

Oct. 27, 2014   (EP) .................................. 14190531

(51) Int. Cl.
   *A61K 8/26*       (2006.01)
   *A61K 8/44*       (2006.01)
   *A61Q 15/00*     (2006.01)
   *C01F 7/56*       (2006.01)
   *A61K 8/19*       (2006.01)
   *A61K 8/02*       (2006.01)
   *A61K 8/92*       (2006.01)

(52) U.S. Cl.
CPC .............. *A61K 8/26* (2013.01); *A61K 8/0229* (2013.01); *A61K 8/19* (2013.01); *A61K 8/44* (2013.01); *A61K 8/922* (2013.01); *A61Q 15/00* (2013.01); *C01F 7/56* (2013.01); *A61K 2800/31* (2013.01); *A61K 2800/48* (2013.01); *C01P 2004/61* (2013.01); *C01P 2006/90* (2013.01)

(58) Field of Classification Search
None
See application file for complete search history.

(56) References Cited

U.S. PATENT DOCUMENTS

| 2,210,013 | A | 8/1940 | Teller |
| 2,412,535 | A | 12/1946 | Richardson et al. |
| 3,666,668 | A | 5/1972 | Klausner |
| 3,766,233 | A | 10/1973 | Tsukada |
| 3,792,068 | A | 12/1974 | Luedders et al. |
| 4,183,911 | A | * | 1/1980 | Smithies .................. A61K 8/11 424/401 |
| 4,359,456 | A | 11/1982 | Gosling et al. |
| 4,369,173 | A | 1/1983 | Causland et al. |
| 4,435,382 | A | 3/1984 | Shin et al. |
| 5,348,731 | A | 9/1994 | Patti et al. |
| 5,681,802 | A | 10/1997 | Fujiwara et al. |
| 5,744,130 | A | * | 4/1998 | Guskey ................ A61K 8/0229 424/66 |
| 5,814,309 | A | 9/1998 | Panitch |
| 5,911,977 | A | 6/1999 | Brewster et al. |
| 5,955,065 | A | * | 9/1999 | Thong ....................... A61K 8/19 424/400 |
| 6,024,945 | A | 2/2000 | Parekh |
| 6,042,816 | A | * | 3/2000 | Shen ......................... A61K 8/19 424/65 |
| 6,096,297 | A | 8/2000 | Jones et al. |
| 6,136,303 | A | 10/2000 | Ruebusch et al. |
| 6,261,543 | B1 | 7/2001 | Fletcher et al. |
| 6,383,476 | B1 | 5/2002 | Scavone et al. |
| 6,511,243 | B2 | 1/2003 | Miranda |
| 6,911,195 | B2 | 6/2005 | Vu et al. |
| 6,942,850 | B2 | 9/2005 | Coe et al. |
| 7,087,220 | B2 | 8/2006 | Li |
| 7,704,531 | B2 | 4/2010 | Tang et al. |
| 9,775,791 | B2 | 10/2017 | Fawzy et al. |
| 9,867,765 | B2 | 1/2018 | Franklin et al. |
| 10,117,814 | B2 | 11/2018 | Court et al. |

(Continued)

FOREIGN PATENT DOCUMENTS

CN        1323191      11/2001
DE      19662878      6/2001

(Continued)

OTHER PUBLICATIONS

Search Report and Written Opinion in PCTEP2018079947; dated Jan. 2, 2019.
Deodorant Roll-On; Deodorant Roll-On Product Data Sheets (D19A-J) ; Apr. 1, 2011; pp. 1-31.
Clinical Protection Antiperspirant Deodorant Cream; Deodorant Cream Product Data Sheets (D20A-D); Sep. 24, 2018; pp. 1-11.
Notice of Opposition in EP14725433 (EP2999452) (P&G); dated Sep. 24, 2018.
Search Report & Written Opinion in PCTEP2015074528; dated Jan. 20, 2016.
Search Report & Written Opinion in PCTEP2015074529; dated Dec. 21, 2015.
Anti-Perspirant Deodorant Roll-On; Mintel GNPD Database; Nov. 1, 2014; pp. 1-2; XP002739560; Germany.

(Continued)

*Primary Examiner* — Issac Shomer
(74) *Attorney, Agent, or Firm* — Greenberg Traurig, LLP

(57) ABSTRACT

Anhydrous antiperspirant stick or soft solid composition comprising an antiperspirant active system, thickening agent, and non-aqueous carrier oil, characterised in that the particulate antiperspirant active system comprises an aluminium sesquichlorohydrate of formula $Al_2(OH)_{4.4}Cl_{1.6}$ to $Al_2(OH)_{4.9}Cl_{1.1}$ activated with a water soluble calcium salt.

10 Claims, No Drawings

(56) References Cited

U.S. PATENT DOCUMENTS

| | | | |
|---|---|---|---|
| 10,398,633 B2* | 9/2019 | Court | A61K 8/26 |
| 2002/0012565 A1 | 1/2002 | Sirna et al. | |
| 2002/0125462 A1 | 9/2002 | McKie et al. | |
| 2003/0049219 A1* | 3/2003 | Lemoine | A61K 8/02 424/66 |
| 2003/0215399 A1 | 11/2003 | Smith et al. | |
| 2003/0215408 A1 | 11/2003 | Dees | |
| 2004/0115147 A1 | 6/2004 | Vu et al. | |
| 2005/0163737 A1 | 7/2005 | Lemoine et al. | |
| 2006/0153788 A1 | 7/2006 | Swaile et al. | |
| 2006/0204463 A1 | 9/2006 | Tang et al. | |
| 2006/0222612 A1 | 10/2006 | Ni et al. | |
| 2007/0020211 A1 | 1/2007 | Li et al. | |
| 2007/0148113 A1 | 6/2007 | Lemoine et al. | |
| 2007/0148443 A1 | 6/2007 | Blum et al. | |
| 2007/0172440 A1 | 7/2007 | Schulz et al. | |
| 2007/0196303 A1 | 8/2007 | Li et al. | |
| 2007/0286830 A1 | 12/2007 | Li et al. | |
| 2007/0292358 A1 | 12/2007 | Emmerling et al. | |
| 2008/0131354 A1 | 6/2008 | Li et al. | |
| 2008/0241089 A1 | 10/2008 | Banowski et al. | |
| 2008/0267895 A1 | 10/2008 | Franklin et al. | |
| 2009/0018044 A1 | 1/2009 | Dreja et al. | |
| 2009/0104281 A1 | 4/2009 | Taylor et al. | |
| 2009/0232746 A1 | 9/2009 | Mateu et al. | |
| 2009/0311195 A1 | 12/2009 | Clark et al. | |
| 2009/0317347 A1 | 12/2009 | Popoff et al. | |
| 2010/0303749 A1 | 12/2010 | Pan | |
| 2011/0038822 A1 | 2/2011 | Phipps et al. | |
| 2011/0038823 A1 | 2/2011 | Phipps et al. | |
| 2011/0038902 A1 | 2/2011 | Phipps et al. | |
| 2011/0217254 A1 | 9/2011 | Miertsch et al. | |
| 2011/0274637 A1 | 11/2011 | Milardovic et al. | |
| 2013/0164238 A1 | 6/2013 | Banowski et al. | |
| 2013/0273274 A1 | 10/2013 | Mueller et al. | |
| 2014/0079649 A1 | 3/2014 | Swaile et al. | |
| 2014/0173833 A1 | 6/2014 | Banowski et al. | |
| 2014/0178321 A1 | 6/2014 | Banowski et al. | |
| 2014/0301963 A1 | 10/2014 | Claas et al. | |
| 2015/0118173 A1 | 4/2015 | Farwick et al. | |
| 2016/0106649 A1 | 4/2016 | Fawzy et al. | |
| 2016/0113850 A1 | 4/2016 | Fawzy et al. | |
| 2018/0140522 A1 | 5/2018 | Doering et al. | |

FOREIGN PATENT DOCUMENTS

| | | |
|---|---|---|
| EP | 0308937 | 3/1989 |
| EP | 0343843 | 11/1989 |
| EP | 0405598 | 1/1991 |
| EP | 0674899 | 10/1995 |
| EP | 1175165 | 4/2000 |
| EP | 1104282 | 6/2001 |
| EP | 1550435 | 7/2005 |
| EP | 1576946 | 9/2005 |
| EP | 2999452 | 12/2017 |
| GB | 811079 | 4/1959 |
| GB | 813767 | 5/1959 |
| GB | 1024501 | 3/1966 |
| GB | 1268200 | 3/1972 |
| GB | 1285073 | 8/1972 |
| GB | 1347950 | 2/1974 |
| GB | 1362495 | 8/1974 |
| GB | 1555044 | 11/1979 |
| GB | 1589229 | 5/1981 |
| GB | 2113116 | 8/1983 |
| GB | 2299507 | 10/1996 |
| JP | 2014047186 | 3/2014 |
| WO | WO9604884 | 2/1996 |
| WO | WO9624326 | 8/1996 |
| WO | WO0001422 | 1/2000 |
| WO | WO0010512 | 3/2000 |
| WO | WO0127351 | 4/2001 |
| WO | WO2005007377 | 1/2005 |
| WO | WP2005018553 | 3/2005 |
| WO | WO2005105026 | 11/2005 |
| WO | WO2006050776 | 5/2006 |
| WO | WO2006062846 | 6/2006 |
| WO | WO2006091417 | 8/2006 |
| WO | WO2007124889 | 11/2007 |
| WO | WO2008063188 | 5/2008 |
| WO | WO2009044381 | 4/2009 |
| WO | WO2009075678 | 6/2009 |
| WO | WO2009076591 | 6/2009 |
| WO | WO2009076592 | 6/2009 |
| WO | WO2011016807 | 2/2011 |
| WO | WO2012010684 | 1/2012 |
| WO | WO2012021356 | 2/2012 |
| WO | WO2012060817 | 5/2012 |
| WO | WO2012061280 | 5/2012 |
| WO | WO2012098189 | 7/2012 |
| WO | 2481392 | 8/2012 |
| WO | WO2012148480 | 11/2012 |
| WO | WO2012148481 | 11/2012 |
| WO | WO2013064367 | 5/2013 |
| WO | WO2013158077 | 10/2013 |
| WO | WO2014095688 | 6/2014 |
| WO | WO2014147739 | 9/2014 |
| WO | WO2014187684 | 11/2014 |
| WO | WO2014187685 | 11/2014 |
| WO | WO2014187802 | 11/2014 |
| WO | WO-2014187802 A1 * 11/2014 ............ A61K 8/062 | |
| WO | WO2014187865 | 11/2014 |
| WO | WO2015091742 | 6/2015 |
| WO | WO2016066528 | 5/2016 |
| WO | WO2016078991 | 6/2016 |
| WO | WO2016198202 | 12/2016 |
| WO | WO2017076836 | 5/2017 |

OTHER PUBLICATIONS

Written Opinion in EP15150655; dated Jun. 22, 2015; European Patent Office (EPO).
Anti-Perspirant Deodorant Roll-on; Mintel GNPD Database; Apr. 1, 2012; pp. 1-2; XP002739559; United Kingdom.
Search Report in EP15150655; dated Jun. 22, 2015; European Patent Office (EPO).
Search Report in EP14190531; dated May 8, 2015.
Written Opinion in EP14190531; dated May 8, 2015.
Written Opinion 1 in PCTEP2014059583; dated Oct. 6, 2014.
Search Report in PCTEP2014059582; dated Oct. 6, 2014.
Written Opinion in PCTEP2014059582; dated Oct. 6, 2014.
Search Report in PCTEP2014059583; dated Oct. 6, 2014.
Written Opinion in PCTEP2014060306; dated Oct. 6, 2014.
Search Report in PCTEP2014060306; dated Oct. 6, 2014.
Search Report in EP14193902; dated May 6, 2015.
Search Report in EP14190530; dated Feb. 12, 2015.
Written Opinion in EP14190530; dated Feb. 12, 2015.
Written Opinion 2 in PCTEP2014059583; dated Apr. 30, 2015.
Written Opinion in EP14193902; dated May 6, 2015.
Amodimethicone; Saapedia; May 21, 2015; pp. 1-3; "www.saapedia.org/en/saa/?type-detail&id-1885".; .; United States of America.
Written Opinion in EP13168417; dated Oct. 31, 2013.
IPRP2 in PCTEP2014059583; dated Sep. 11, 2015.
Search Report in EP13168418; dated Oct. 31, 2013.
Search Report in EP13168417; dated Oct. 31, 2013.
Written Opinion 2 in PCTEP2014060306; dated May 8, 2015.
IPRP2 in PCTEP2014060306; dated Sep. 16, 2015.
Laden; Antiperspirants and Deodorants 1999 2nd Edition pp. 96-97; Antiperspirants and Deodorants 1999 2nd Edition pp. 96-97; 1999; pp. 96-97; 2nd Edition.
Written Opinion in EP13168418; dated Oct. 31, 2013.
Anonymous; Aluminum Zirconium Chlorohydrex Complexes with Glycine; Cosmeticsinfo.org; 2015; pp. 1-3 Retrieved from the Internet: http://www.cosmeticsinfo.org/ingredient/aluminum-zirconium-chlorohydrex-complexes-glycine [retrieved on Dec. 7, 2015] XP055234010.
Search Report & Written Opinion in PCTEP2015075419; dated Jan. 21, 2016.

(56) References Cited

OTHER PUBLICATIONS

Search Report & Written Opinion in PCTEP2015076365; dated Feb. 11, 2016.
Apr. 2014 Teacher's Guide for (Under) Arm Yourself with Chemistry?; acs.orgichemmatters; Apr. 2014; pp. 1-38 Retrieved from Internet: http://www.acs.org/content/dam/acsorg/education/resources/highschool/chemmatters/teacherguide/chemmatters-tg-april2014-deodorant.doc retrieved Dec. 7, 2015 XP055234066
Search Report & Written Opinion in EP15193404; dated May 9, 2016; European Patent Office (EPO).
Search Report & Written Opinion in EP15193409; dated Apr. 18, 2016.
Search Report & Written Opinion in EP15193410; dated May 19, 2016.
Portective Deodorant Spray; Database GNPD Mintel; 2014; pp. 1-2; XP002756659; Mexico.
Written Opinion in PCTEP2015074529; dated Sep. 2016.
Search Report and Written Opinion in PCTEP2016076311; dated Dec. 23, 2016.
Pluronic(R) F-127; Newdruginfo.com; Jun. 7, 2016; 1 page.
Search Report and Written Opinion in PCTEP2016073661; dated Dec. 5, 2016.
Search Report and Written Opinion in PCTEP2016076306; dated Jan. 23, 2017.
Protective Deodorant Spray; Mintel GNPD; 2014; pp. 1-2; XP002756659.
Search Report & Written Opinion in PCTEP2016080034; dated Feb. 9, 2017.
IRPR2 in PCTEP2015074528; dated Jan. 18, 2017.
Search Report and Written Opinion in EP17199987; dated Dec. 2, 2016.
Written Opinion 2 in PCTEP2016076306; dated Sep. 14, 2017.
Search Report and Written Opinion in EP17199987; dated Dec. 6, 2017.
IPRP2 in PCTEP2016073661; dated Oct. 27, 2017.
Karl Laden; Chemistry of Aluminum-Zirconium-Glycine (AZG) Complexes; Antiperspirants and Deodorants; 1999; pp. cover pages, title pages & p. 137 (total of 4 pages); vol. 20, Second Edition.
IPRP in PCTEP2016080034 ; dated Feb. 14, 2018.
Search Report and Written Opinion in EP17200556; dated Apr. 11, 2018.
IPRP2 in PCTEP2016076306; dated Dec. 4, 2017.
Search Report and Written Opinion in EP18164854; dated Jul. 30, 2018.
Search Report and Written opinion in PCTEP2019055000; dated Apr. 3, 2019.
Mintel GNPD; Sensitive Skin Deodorant Spray, Lactovit; Mintel GNPD; Jul. 2013; pp. 1-3, Record ID 2102829.
Mintel GNPD; Protective Deodorant, Lactovit Activit; Mintel GNPD; Sep. 2013; pp. 1-3 Record ID 2192256.
Mintel GNPD; Repairing Deodorant, Lactoit Lacourea 10; Mintel GNPD; Aug. 2014; pp. 1-2 Record ID 2619709.
Mintel GNPD; Deodorant Extra-Efficiency, Lactovit Original; Mintel GNPD; Jul. 2013; pp. 1-2 Record ID2121626.
Edited by Barel, et al.; Handbook of Cosmetic Sience and Technology; Handbook of Cosmetic Sience and Technology; Apr. 9, 2014; pp. 1-2 (Cover & summary); 4th Edition.
Edited by Barel, et al.; Section 48—Antiperspriants and Section 49—Deodorants; Handbook of Cosmetic Science and Technology; Apr. 9, 2014; pp. 1-19 (cover pp and pp. 505-518; 4th Ed.
Regulations; Official Journal of the European Union; Mar 9, 2012; pp. 1-295 or L83/1-L83/295.

* cited by examiner

ANHYDROUS ANTIPERSPIRANT COMPOSITIONS

This application is a national phase filing under 35 USC 371 of International Application No. PCT/EP2015/074528, filed on Apr. 20, 2017, which claims priority from European Patent Application No. 14190531.5 filed Oct. 27, 2014, the contents of which are incorporated herein in their entirety for all purposes.

The present invention is concerned with antiperspirant compositions and with methods of making the same. It is particularly concerned with anhydrous stick and soft solid compositions comprising aluminium sesquichlorohydrate antiperspirant actives.

Certain activated basic aluminium chloride (herein BAC) actives are commercially available and their preparation and use are disclosed in numerous publications.

Traditionally, activated BAC samples have been prepared by prolonged heating of BAC solutions followed by spray drying; see, for example, U.S. Pat. No. 4,359,456 (Gosling). The samples prepared by this method needed to be formulated into essentially anhydrous compositions in order for the antiperspirant to maintain its high activity.

Activated BAC samples have also been prepared using water soluble calcium acids, particularly with a further adjunct such as an amino acid, hydroxyl acid, or betaine. Some of these samples could be formulated into aqueous compositions without the antiperspirant losing all of its enhanced activity.

EP 1,104,282 (Gillette) discloses a means of producing activated BAC samples using a water soluble calcium salt and an amino acid or a hydroxy acid.

U.S. Pat. No. 6,911,195 (Gillette) discloses water-in-oil emulsion gels comprising aluminium-zirconium antiperspirant salts activated using calcium ions.

U.S. Pat. No. 5,955,065 (Gillette) discloses anhydrous suspension formulations comprising particulate BAC and aluminium-zirconium antiperspirant salts activated using calcium ions.

U.S. Pat. No. 6,942,850 (Gillette) discloses aqueous alcoholic composition comprising aluminium-zirconium antiperspirant salts activated using calcium ions.

WO 2009/044381 (P&G) discloses water-in-oil emulsion sticks comprising BAC and aluminium-zirconium antiperspirant salts activated using calcium ions.

U.S. Pat. No. 7,704,531 (Colgate) discloses compositions comprising an active system made from combining an aluminium or aluminium-zirconium salt, a calcium salt, and a betaine.

US 2011/0038823 (Dial/Henkel) discloses water-in-oil emulsion sticks comprising an antiperspirant active prepared by combining BAC, calcium chloride and glycine.

US 2007/196303, US 2007/0020211, WO 2008/063188, US 2008/0131354 and U.S. Pat. No. 7,087,220 (Summit and Reheis) each describe methods of making calcium-activated antiperspirant salts.

WO 2009/075678, WO 2009/076592, WO 2011/016807, WO 2012/060817, WO 2012/061280, WO 2012/148480 and WO 2012/148481 (Colgate) disclose the manufacture of activated antiperspirant salts by neutralisation of aluminium chloride with calcium hydroxide in the presence of glycine.

The present invention is particularly concerned with BAC compositions comprising aluminium sesquichlorohydrate (herein ASCH) of chemical formula $Al_2(OH)_{4.4}Cl_{1.6}$ to $Al_2(OH)_{4.9}Cl_{1.1}$. This material is commercially available, but its formulation and use described herein are new and deliver unexpected benefits.

In a first aspect of the present invention, there is provided an anhydrous antiperspirant stick or soft solid composition comprising an antiperspirant active system, thickening agent, and non-aqueous carrier oil, characterised in that the particulate antiperspirant active system comprises an aluminium sesquichlorohydrate of formula $Al_2(OH)_{4.4}Cl_{1.6}$ to $Al_2(OH)_{4.9}Cl_{1.1}$ activated with a water soluble calcium salt.

In a second aspect of the present invention, there is provided a method of manufacture of a composition according to the first aspect of the invention.

In a third aspect of the present invention, there is provided a method of attaining an antiperspirant benefit comprising the topical application to the surface of the human body of a composition according to the first aspect of the invention.

The choice of BAC salt used is critical to the success of the present invention. We have found that surprisingly good results are found on using BAC salts commonly referred to as aluminium sesquichlorohydrate (herein ASCH) having the chemical formula $Al_2(OH)_{4.4}Cl_{1.6}$ to $Al_2(OH)_{4.9}Cl_{1.1}$. Most commercial ASCH samples are of chemical formula $Al_2(OH)_{4.7}Cl_{1.3}$ to $Al_2(OH)_{4.9}Cl_{1.1}$ and it is preferred to use ASCH salts of this formula.

The surprisingly good results referred to in the above paragraph include surprisingly good antiperspirancy performance. In addition, compositions prepared according to the present invention have remarkable storage stability, maintaining their good performance for many months.

The BAC salt used in the present invention has aluminium to chloride molar ratio of from 1.25:1 to 1.82:1 and preferably 1.54:1 to 1.82:1.

The present invention involves the "activation" of ASCH by a water soluble calcium salt and preferably an amino acid.

In order for the ASCH to become activated, it is important to have sufficient calcium present relative to the amount of aluminium present. The molar ratio of calcium to aluminium is typically at least 1:40, preferably at least 1:30 and more preferably at least 1:20. It is not advantageous to have the calcium concentration in excess of the aluminium concentration, indeed it is preferred that the calcium concentration is no more than half that of the aluminium concentration and more preferred that it is no more than a fifth of said concentration. For the preferred molar ratios of calcium to aluminium of at least 1:40 and at least 1:20, it is independently preferred that this ratio is no greater than 1:2 and more preferred that it is no greater than 1:5.

In particularly preferred embodiments, the molar ratio of calcium to aluminium is at least 1:15 and preferably no greater than 1:5 and in especially preferred embodiments it is at least 1:10 and preferably no greater than 1:5.

A preferred water soluble calcium salt for use in the present invention is calcium chloride.

Herein, references to molar amounts and ratios of "aluminium" are calculated on the basis of mono-nuclear aluminium, but include aluminium present in poly-nuclear species; indeed, most of the aluminium in the salts of relevance is present in poly-nuclear species.

In preferred embodiments, an amino acid is also used to activate the ASCH. The molar ratio of amino acid to aluminium is preferably at least 1:20, more preferably at least 1:10 and most preferably at least 1:5. It is not advantageous to have the amino acid concentration in excess of the aluminium concentration; hence, the molar amino acid to aluminium is preferably from 1:20 to 1:1, more preferably from 1:10 to 1:1 and most preferably from 1:5 to 1:1.

In particularly preferred embodiments, the molar ratio of amino acid to aluminium is at least 1:4 and preferably no greater than 1:1 and in especially preferred embodiments it is at least 1:3 and preferably no greater than 1:1.

The presence of both calcium and amino acid is highly preferred for the success of the present invention. In preferred embodiments, the molar ratio of calcium to aluminium is at least 1:40 and the molar ratio of amino acid to aluminium is at least 1:20. In further preferred embodiments the molar ratio of calcium to aluminium is at least 1:20 and the molar ratio of amino acid to aluminium is at least 1:10. In particularly preferred embodiments the molar ratio of calcium to aluminium is from 1:20 to 1:5 and the molar ratio of amino acid to aluminium is from 1:10 to 1:1.

In certain especially preferred embodiments, the molar ratio of calcium to aluminium is from 1:15 to 1:5 and the molar ratio of amino acid to aluminium is from 1:4 to 1:1. In these especially preferred embodiments, exemplary performance in is obtained when the molar ratio of calcium to aluminium is from 1:10 to 1:5 and the molar ratio of amino acid to aluminium is from 1:3 to 1:1.

The above indicated preferences for calcium to aluminium molar ratio and/or amino acid to aluminium molar ratio lead to compositions of higher Band III content (vide infra) and, in general, higher antiperspirancy performance. It will be noted that higher Band III content is generally indicative of higher antiperspirancy performance.

The activation process generally produces a mixture of aluminium species having a relatively high content of what is commonly termed Band III material, as determined by SEC (Size Exclusion Chromatography) analysis. The SEC technique employed is well known in the art and is described in further detail in U.S. Pat. No. 4,359,456 (Gosling). The SEC band commonly referred to as Band III is designated as "Peak 4" in EP 1,104,282 B1 by Gillette.

Herein, "Band III content" refers to the integrated area in the Band III region of the SEC chromatograph relative to the total integrated area in all of the regions corresponding to aluminium species; that is to say, Bands I, II, III, and IV.

In preferred embodiments of the invention, the aluminium sesquichlorohydrate in the particulate antiperspirant active system has a Band III content of at least 40%; in particularly preferred embodiments, the Band III content of the aluminium sesquichlorohydrate is at least 55%.

In the activation process and method of manufacture described herein, it is preferred that the activation mixture is heated sufficiently for the Band III content of the aluminium species to become at least 40% and more preferably at least 55%.

The method of manufacture described herein involves the production an aqueous solution of an activated antiperspirant salt. Such solutions are then dried, typically by spray-drying and the resulting powder incorporated in a composition according to the invention.

Hence, the particulate antiperspirant active used in the present invention may typically be considered to be a co-spray-dried mixture of (i) aluminium sesquichlorohydrate of formula $Al_2(OH)_{4.4}Cl_{1.6}$ to $Al_2(OH)_{4.9}Cl_{1.1}$ activated by calcium chloride and (ii) the calcium chloride used to achieve said activation. Preferably, the antiperspirant active may be considered to be a co-spray-dried mixture of (i) aluminium sesquichlorohydrate of formula $Al_2(OH)_{4.4}Cl_{1.6}$ to $Al_2(OH)_{4.9}Cl_{1.1}$ activated by calcium chloride and an amino acid and (ii) the calcium chloride and amino acid used to achieve said activation.

The method of manufacture typically involves a solution of aluminium sesquichlorohydrate of formula $Al_2(OH)_{4.4}Cl_{1.6}$ to $Al_2(OH)_{4.9}Cl_{1.1}$ being heated with a water soluble calcium salt to achieve a Band III content of at least 50% before being spray dried to give a powder which is subsequently formulated with a suspending agent, carrier oil and liquefied propellant gas.

In a preferred method of manufacture as described in the above paragraph, the aluminium sesquichlorohydrate is also heated with an amino acid. In a particularly preferred aspect of this method, the aluminium sesquichlorohydrate is heated to achieve a Band III content of at least 60%.

The spray-dried powder produced from the aqueous solution of an activated antiperspirant salt as described above is the particulate antiperspirant active system comprising a water soluble calcium salt and an aluminium sesquichlorohydrate of formula $Al_2(OH)_{4.4}Cl_{1.6}$ to $Al_2(OH)_{4.9}Cl_{1.1}$ as described in the first aspect of the invention.

The particulate antiperspirant active system preferably has a mean particle size (D50) of from 2 to 30 microns, more preferably from 2 to 20 microns, and most preferably from 2.5 to 10 microns. Such compositions have been found to give surprisingly good antiperspirancy performance and also have good sensory properties.

Herein, mean (D50) particle sizes may be measured using (laser) light scattering techniques, for example using a Mastersizer instrument, obtainable from Malvern Instruments. Such instruments are set to produce a volume plot and a lens is selected in accordance with the makers instructions to accommodate the expected particle size distribution, (or various lenses can be tested until the best lens is identified). Measurements are made by methods known in the art.

The particulate antiperspirant active system is preferably spray-dried using rotary atomisation.

The compositions of the present invention are anhydrous, having less than 2% by weight of free water, preferably less than 1% by weight of free water, more preferably less than 0.5% free water and most preferably less than 0.1% free water.

Herein, "free water" excludes any water of hydration associated with the antiperspirant salt or other solid component added to a particular composition, but includes all other water present.

Herein, references to amounts of components such as "carrier oil" or "thickening agent" relate to the total amount of such components present in the composition.

Other non-essential components may also be including in compositions according to the invention.

Herein, amounts and concentrations of ingredients are percentages by weight of the total composition, unless otherwise indicated and ratios are ratios by weight, unless otherwise indicated.

Herein, unless the context demands otherwise, all weights, %s, and other numbers can be qualified by the term "about".

Compositions according to the present invention have a certain hardness in order for them to be used a sticks or soft solids.

The "hardness" of stick and soft solid compositions refers to the depth, in millimetres, that a cone penetrates into a test specimen under fixed conditions, as determined in accordance with the procedures of ASTM Method D217-48, incorporated herein by reference, using a Petrotest PNR10 Penetrometer (or equivalent), equipped with an ASTMD2884 plunger (Petrotest Cat. #18-0081 or equivalent, weight=47.5 g) and a 2.5 g aluminium cone, 20° angle with a base diameter of 10 mm, wherein hardness values are reported as an average of 6 replicate measurements.

Compositions according to the present invention typically have a hardness of less than 30 mm, preferably less than 25 mm and more preferably less than 20 mm.

Soft solid compositions according to the present invention typically have a hardness value of from 5 to 25 mm, more particularly from 10 to 20 mm.

Stick compositions according to the present invention typically have a hardness value of less 20 mm and preferably less than 15 mm. Particularly preferred stick compositions have a hardness of from 7.5 to 12.5 mm.

An essential component of compositions of the invention is carrier oil. In preferred embodiments, this may also be a masking oil, serving the purpose of reducing visible deposits when the composition accidentally comes into contact with clothing, for example.

Herein, the terms "oil" and signifies a water-insoluble organic material that is liquid at 20° C. Any material having a solubility of less than 0.1 g/100 g at 20° C. is considered to be insoluble.

A preferred optional component for use in accordance with the present invention is a fragrance oil, sometimes alternatively called a perfume oil. The fragrance oil may comprise a single fragrance or component more commonly a plurality of fragrance components. Herein, fragrance oils impart an odour, preferably a pleasant odour, to the composition. Preferably, the fragrance oil imparts a pleasant odour to the surface of the human body the composition is applied to the same.

The amount of fragrance oil in the composition is commonly up to 3% advantageously is at least 0.5% and particularly from 0.8% to 2%.

The total amount of carrier oil in the composition may be from 5% to 95%, but is preferably from 10 to 90% and more preferably from 15 to 85%.

As fragrance oil may also serve as carrier oil, it should also be included as carrier oil in calculating the amount of this latter component present in the composition.

The carrier oil may be selected from any of those known in the art, although hydrophobic carrier oils are preferred.

A preferred class of carrier oil are silicone oils, that is to say, liquid polyorganosiloxanes. Such materials may be cyclic or linear, examples include Dow Corning silicone fluids 344, 345, 244, 245, 246, 556, and the 200 series; Union Carbide Corporation Silicones 7207 and 7158; and General Electric silicone SF1202.

Suitable carrier oils can be selected from alkyl ether oils having a boiling point of above 100° C. and especially above 150° C., including polyalkyleneglycol alkyl ethers. Such ethers desirably comprise between 10 and 20 ethylene glycol or propylene glycol units and the alkyl group commonly contains from 4 to 20 carbon atoms. The preferred ether oils include polypropylene glycol alkyl ethers such as PPG-14-butylether and PPG-15-stearyl ether.

Suitable carrier oils can include one or more triglyceride oils. The triglyceride oils commonly comprise the alkyl residues of aliphatic $C_7$ to $C_{20}$ alcohols, the total number of carbon atoms being selected in conjunction with the extent of olefinic unsaturation and/or branching to enable the triglyceride to be liquid at 20° C. One example is jojoba oil. Particularly preferably, in the triglyceride oil the alkyl residues are linear $C_{18}$ groups having one, two or three olefinic degrees of unsaturation, two or three being optionally conjugated, many of which are extractable from plants (or their synthetic analogues), including triglycerides of oleic acid, linoleic acid, conjugated linoleic acids, linolenic acid, petroselenic acid, ricinoleic acid, linolenelaidic acid, trans 7-octadecenoic acid, parinaric acid, pinolenic acid, punicic acid, petroselenic acid and stearidonic acid.

Suitable carrier oils can include those derived from unsaturated $C_{18}$ acids, including coriander seed oil, impatiens balsimina seed oil, parinarium laurinarium kernel fat oil, sabastiana brasilinensis seed oil, dehydrated castor seed oil, borage seed oil, evening primrose oil, aquilegia vulgaris oil, sunflower (seed) oil and safflower oil. Other suitable oils are obtainable from hemp, and maize corn oil. An especially preferred oil by virtue of its characteristics is sunflower (seed) oil.

Further suitable carrier oils, that can also be emollient oils, comprise alkyl or alkyl-aryl ester oils having a boiling point of above 150° C. (and a melting point of below 20° C.). Such ester oils include oils containing one or two alkyl groups of 12 to 24 carbon atoms length, including isopropyl myristate, isopropyl palmitate and myristyl palmitate. Other non-volatile ester oils include alkyl or aryl benzoates such $C_{12-15}$ alkyl benzoate, for example Finsolv TN™ or Finsolv Sun™.

A further class of suitable carrier oils comprises non-volatile dimethicones, often comprising phenyl or diphenylene substitution, for example Dow Corning 200 350 cps or Dow Corning 556.

A further essential component of compositions of the invention is a thickening agent, sometimes alternatively referred to as a gelling agent or gellant. Such agents increase the viscosity of or solidify the carrier oil in which the particulate antiperspirant active is typically suspended.

The thickening agent may be selected from any of those known in the art. Often, the thickening agent includes a wax. Waxes typically are considered to melt at above 40° C. and particularly between 55 and 95° C. Waxes can include ester waxes, including C12 to C24 linear fatty alcohols, waxes obtained from animals or plants, often after hydrogenation, silicone elastomers and silicone waxes. The thickening agent can comprise a mixture of particulate thickening agents, a mixture of waxes or a mixture of both types of material.

The proportion of thickening agent thickening agents is often selected in the range of from 1:30 to 1:12.5 parts per part by weight of carrier oil.

The thickening agents used in compositions according to the invention, and especially stick compositions according to the invention, are preferably selected from fibre-forming non-polymeric gelling agents and waxes, optionally supplemented by particulate silica and/or an oil-soluble polymeric thickening agent.

Waxes employed herein as thickening agents are often selected from hydrocarbons, linear fatty alcohols, silicone polymers, esters of fatty acids or mixtures containing such compounds along with a minority (less than 50% w/w and often less than 20% w/w) of other compounds. Naturally occurring waxes are often mixtures of compounds which include a substantial proportion of fatty esters.

Examples of hydrocarbon waxes include paraffin wax, ozakerite, microcrystalline wax and polyethylene wax, the last named desirably having an average molecular weight of from 300 to 600 and advantageously from 350 to 525.

Linear fatty alcohols commonly contain from 14 to 40 carbon atoms and often from 16 to 24. Preferred thickening agents of this class are stearyl alcohol and behenyl alcohol, with stearyl alcohol being especially preferred.

Examples of ester waxes include esters of $C_{16}$-$C_{22}$ fatty acids with glycerol or ethylene glycol, which can be isolated from natural products or more conveniently synthesised from the respective aliphatic alcohol and carboxylic acid.

Examples of natural waxes include beeswax, wool wax and spermaceti wax of animal origin, and caster wax, jojoba wax, carnauba wax and candelilla wax which are of vegetable origin. Montan wax, which is an example of mineral wax, includes non-glyceride esters of carboxylic acids, hydrocarbons and other constituents.

Further waxes employable herein comprise silicone polymer waxes, including waxes which satisfy the empirical formula:

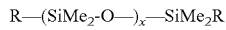

R—(SiMe$_2$-O—)$_x$—SiMe$_2$R in which x is at least 10, preferably 10 to 50 and R represents an alkyl group containing at least 20 carbons, preferably 25 to 40 carbons, and particularly having an average linear chain length of at least 30 carbons.

Other silicone waxes comprise copolymers of dimethicone and alkyloxymethicone, satisfying the general formula:—

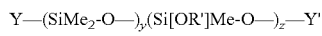

Y—(SiMe$_2$-O—)$_y$(Si[OR']Me-O—)$_z$—Y' in which Y represents SiMe$_2$-O, Y'SiMe$_2$, R' an alkyl of at least 15 carbons preferably 18 to 22 such as stearyl, y and z are both integers, totaling preferably from 10 to 50.

Waxes useful in the present invention will generally be those found to thicken cylcomethicone, when dissolved therein at a concentration of 5 to 15% by weight.

Fibre-forming thickening agents are dissolved in the carrier oil at elevated temperature and on cooling precipitate out to form a network of very thin strands that structure, i.e. thicken, the carrier oil. One particularly effective category comprises N-acyl aminoacid amides and in particular linear and branched N-acyl glutamic acid dialkylamides, such as in particular N-lauroyl glutamic acid di n-butylamide and N-ethylhexanoyl glutamic acid di n-butylamide and especially mixtures thereof. Such amido gellants can be employed in anhydrous compositions according to the present invention, if desired, with 12-hydroxystearic acid.

Other amido SMGAs include 12-hydroxystearic acid amides, and amide derivatives of di and tribasic carboxylic acids as set forth in WO 98/27954, including notably alkyl N,N'dialkyl succinamides.

Further suitable amido-containing thickening agents are described in U.S. Pat. Nos. 6,410,003, 7,332,153, 6,410,001. U.S. Pat. Nos. 6,321,841, and 6,248,312.

The thickening agent is typically employed in the composition at a concentration of from 1.5 to 30%. When a fibre-forming thickening agent is employed, its concentration is typically in the range of from 1.5 to 15%. When a wax is employed, its concentration is usually selected in the range of from 10 to 30%, and particularly from 12 to 24% w/w. Some highly desirable compositions comprise in combination a first thickening agent with a second thickening agent.

One category of oil-soluble polymer thickening agent which has been found suitable is a polysaccharide esterified with a mono-carboxylic acid containing at least 12 carbon atoms, and preferably a dextrin fatty acid ester such as dextrin palmitate or dextrin stearate. Commercial products are available under the trade mark Rheopearl.

A second category of polymer thickening agent comprises polyamides for example those discussed in U.S. Pat. No. 5,500,209 or 6,353,076.

A third category of thickening agent comprises block copolymers of styrene with ethylene propylene and/or butylene available under the trade name KRATON, and particularly styrene ethylene/butylene styrene linear block copolymers. A related category of thickening polymer comprises polymers of alpha methylstyrene and styrene, such as those under the trade name KRISTALEX, eg KRISTALEX F85 having a mean molecular weight of approximately 1200. Yet another thickening polymer comprises alkyl substituted galactomannan available under the trade name N-HANCE AG.

A still further class of thickening polymers co-polymers of vinyl pyrrolidone with polyethylene containing at least 25 methylene units, such as triacontanyl polyvinylpyrrolidone, under the trade name Antaron WP-660.

Such thickening polymer is often employed in a weight ratio to the oil blend that is selected in the range of from 1:30 to 1:5, taking into account the hardness of the soft solid that is desired, the inherent ability of the chosen polymer to increase viscosity and the presence or otherwise of an additional thickening agent.

A further class of material which is well suited to forming or contributing to the formation of soft solid compositions comprises silicone elastomers. Commonly, the elastomer is non-emulsifying and especially is a dimethicone/vinyldimethicone cross polymer. Such materials commonly supplied as a dispersion of the active material in cyclomethicone fluid or a non-volatile oil, typically at a concentration in the region of 10 to 20% by weight. Such elastomers are desirably present at a concentration of from 1 to 10% by weight of the composition.

A thickening agent especially well suited to forming or contributing to the formation of a soft solid composition comprises particulate silica and especially fumed silica. It is desirable to include at least 2% and especially at least 2.5% by weight of the silica in the composition, such as in the range of up to 10% by weight.

Other components that may be included in compositions according to the invention including those described in the following paragraphs.

Wash-off agents may be included, often in an amount of up to 10%, to assist in the removal of the formulation from skin or clothing. Such wash-off agents are typically non-ionic surfactants such as esters or ethers containing a C$_8$ to C$_{22}$ alkyl moiety and a hydrophilic moiety comprising a polyoxyalkylene group (POE or POP).

Skin feel improvers (e.g. talc or finely divided high molecular weight polyethylene), may be included, typically in an amount from 1 up to 10%.

Skin moisturisers, such as glycerol or polyethylene glycol (e.g. mol. wt. 200 to 600) may be included, typically in an amount of up to 5%.

Skin benefit agents, such as allantoin or lipids, may be included, typically in an amount of up to 5%.

A highly preferred optional component is a preservative, such as ethyl or methyl parabens or BHT (butyl hydroxy toluene), typically in an amount of from 0.01 to 0.1%.

Fragrance (vide supra) is also a highly optional component. Fragrance may be present as free oils or it may be present in encapsulated form.

EXAMPLES

In the following examples, all percentages are by weight, unless otherwise indicated.

The ASCH used was approximately 80% anhydrous ASCH solids (and 20% water) and was obtained from Summit as Reach 301.

The ASCH used was activated with calcium chloride and glycine and treated as follows. 30 parts of Reach 301 powder, 4.0 parts calcium chloride dihydrate and 9.4 parts glycine were combined with 56.6 parts water. 60 L of this solution was heated at 85° C. and then maintained at this temperature for 5 hours in a corrosion resistant 70 L vessel.

The resulting solution was spray-dried using a large scale spray dryer (inlet temperature 290+/−5°, outlet temperature 117+/−2°, rotary atomisation).

The particulate AASCH obtained from the above process had a mean (D50) particle size of 27 microns, a Band III content of 66%, and a ratio of Band II to Band III of 1:7.13. It comprised 19.3% Al, 2.8% Ca, and 26.0% glycine. This powder was jet milled to give a mean (D50) particle size of 4.3 microns. The milling resulted in an increase in the water content of the powder of from 3.3% to 7.5%.

The powder resulting from the above processes was formulated with the other components indicated in Table 1 by methods known in the art to give Examples 1 to 4, varying only in the amount of AASCH employed.

Comparative Example A was also prepared by methods known in art, using a commercially available activated zirconium aluminium glycinate (AZAG) antiperspirant active (Reach 908, ex Summit) at 25%, i.e. equivalent to the AASCH level used in Example 2.

TABLE 1

Examples 1 to 4 and Comparative Example A

| Component | | Example | | | | |
|---|---|---|---|---|---|---|
| Chemical name | Trade name | 1 | 2 | 3 | 4 | A |
| AASCH[1] | | 30.0 | 25.0 | 17.5 | 10.0 | — |
| AZAG | Reach 908 | — | — | — | — | 25.0 |
| Cyclomethicone | DC 245 | 24.75 | 29.75 | 37.25 | 44.75 | 29.75 |
| $C_{12-15}$ alkyl benzoate | Finsolv TN | 13.75 | 13.75 | 13.75 | 13.75 | 13.75 |
| PPG-14 butyl ether | Fluid AP | 8.0 | 8.0 | 8.0 | 8.0 | 8.0 |
| Stearyl alcohol | Lanette C18 Deo. | 18.0 | 18.0 | 18.0 | 18.0 | 18.0 |
| Castor wax | MP80 | 3.5 | 3.5 | 3.5 | 3.5 | 3.5 |
| Polyethylene wax | Performalene 400 | 1.0 | 1.0 | 1.0 | 1.0 | 1.0 |
| Fragrance | Parfum | 1.0 | 1.0 | 1.0 | 1.0 | 1.0 |
| SWR (%) vs. A | | +31 | +27 | +14 | −7 | 0 |

Sweat Weight Reduction (SWR) results were obtained for each Example in direct comparison with a standard AZAG stick product (Comparative Example A) using a test panel of 30 female volunteers. Test operators applied ca. 0.3 g of Example 1, 2, 3, or 4 to one axilla and Comparative Example A (ca 0.3 g) to the other axilla of each panellist. This was done once each day for three days for each comparison. After the third application, panellists were requested not to wash under their arms for the following 24 hours.

24 hours after the third and final product application, the panellists were induced to sweat in a hot-room at 40° C. (±2° C.) and 40% (±5%) relative humidity, for 40 minutes. After this period, the panellists left the hot-room and their axillae were carefully wiped dry. Pre-weighed cotton pads were then applied to each axilla of each panellist and the panellists re-entered the hot-room for a further 20 minutes. Following this period, the pads were removed and re-weighed, enabling the weight of sweat generated to be calculated.

The SWR for each panellist was calculated as a percentage (% SWR) and the mean % SWR was calculated according to the method described by Murphy and Levine in "Analysis of Antiperspirant Efficacy Results", J. Soc. Cosmetic Chemists, 1991 (May), 42, 167-197.

From the results in Table 1 it can be seen that the stick with 25% AASCH (Example 2) gave a SWR reduction that was 27% greater than the standard AZAG stick product, a remarkable result. Also, a stick with only 17.5% AASCH (Example 3) gave a SWR reduction that was marginally better the standard AZAG stick product.

The soft solid compositions detailed in Table 2 (Examples 5 to 9) may be prepared using the same AASCH as used for Examples 1 to 4, using methods known in the art.

TABLE 2

Examples 5 to 9

| | Example | | | | |
|---|---|---|---|---|---|
| Chemical name | 5 | 6 | 7 | 8 | 9 |
| AASCH | 28.0 | 26.3 | 25.0 | 20.0 | 20.0 |
| Cyclopentasiloxane | To 100 | To 100 | To 100 | To 100 | To 100 |
| Silicone elastomer[1] | 4.0 | 4.0 | 4.0 | 4.0 | 4.0 |
| Fumed silica | 1.0 | 1.0 | 1.0 | 1.0 | 1.0 |
| Dimethicone (350 mPa.s) | — | 5.0 | — | 5.0 | 10.0 |
| PPG-14 butyl ether | 10.0 | 5.0 | — | — | — |
| $C_{12-15}$ alkyl benzoate | — | — | 10.0 | 5.0 | — |
| Sunflower seed oil | 0.5 | 0.5 | 0.5 | 0.5 | 0.5 |
| Microcrystalline wax (MP 80-87° C.) | 3.5 | 3.5 | 3.5 | 3.5 | 3.5 |
| Paraffin wax (MP 60-62° C.) | 3.5 | 3.5 | 3.5 | 3.5 | 3.5 |
| Fragrance | 0.8 | 0.8 | 0.8 | 0.8 | 0.8 |

[1]DC9040, ex Dow Dorning. 70-90% Cyclopentasiloxane.

The invention claimed is:

1. An anhydrous antiperspirant stick or soft solid composition comprising an antiperspirant active system, thickening agent, and non-aqueous carrier oil, characterised in that the particulate antiperspirant active system is composed of a water soluble calcium salt, an amino acid and an aluminium sesquichlorohydrate of formula $Al_2(OH)_{4.7}Cl_{1.3}$ to $Al_2(OH)_{4.9}Cl_{1.1}$ heat activated with a water soluble calcium salt and an amino acid, wherein the aluminium sesquichlorohydrate in the antiperspirant active system has a molar ratio of calcium to aluminium of at least 1:20 and a molar ratio of amino acid to aluminium of at least 1:10 and wherein the particulate antiperspirant active system has a mean particle size (D50) of from 2 to 30 microns, wherein the antiperspirant active system is present in a concentration of 10% to 25%, by weight of the composition, an wherein the amino acid is glycine. d 2. The composition according to claim 1, wherein the aluminium sesquichlorohydrate in the antiperspirant active system has a Band III content of at least 40%.

3. The composition according to claim 1, wherein the aluminium sesquichlorohydrate in the antiperspirant active system has a molar ratio of calcium to aluminium of at least 1:15 and the molar ratio of amino acid to aluminium of at least 1:4.

4. The composition according to claim 1, wherein the water soluble calcium salt is calcium chloride.

5. The composition according to claim 1, wherein the aluminium sesquichlorohydrate in the particulate antiperspirant active system has a Band III to Band II ratio of 5:1 or greater.

6. The composition according to claim 1 wherein the particulate antiperspirant active system has a mean particle size (D50) of from 2 to 10 microns.

7. The composition according to claim 1 wherein the composition is in the form of an anhydrous antiperspirant stick.

8. A method of manufacture of an antiperspirant composition according to claim 1, wherein a solution of aluminium sesquichlorohydrate of formula $Al_2(OH)_{4.7}Cl_{1.3}$ to $Al_2(OH)_{4.9}Cl_{1.1}$ is heated with a water soluble calcium salt to achieve a Band III content of at least 40% before being spray dried to give a powder which is subsequently formulated with thickening agent and non-aqueous carrier oil to give a composition having a penetration force value of at least 500 gram-force, wherein both calcium and amino acid are present and the molar ratio of calcium to aluminium is at least 1:20 and the molar ratio of amino acid to aluminium is at least 1:10.

9. The method according to claim 8, wherein the solution of aluminium sesquichlorohydrate of formula $Al_2(OH)_{4.7}Cl_{1.3}$ to $Al_2(OH)_{4.9}Cl_{1.1}$ is heated with a water soluble calcium salt and an amino acid to achieve a Band III content of at least 60% before it is spray dried.

10. The method according to claim 8, wherein the water soluble calcium salt is calcium chloride.

* * * * *